United States Patent [19]

Vorpahl et al.

[11] Patent Number: 5,071,774

[45] Date of Patent: * Dec. 10, 1991

[54] MULTIPARAMETER PARTICLE ANALYSIS

[75] Inventors: John Vorpahl, Livermore; Vartan Ghazarossian, Menlo Park; Edwin F. Ullman, Atherton, all of Calif.

[73] Assignee: Syntex (U.S.A.) Inc., Palo Alto, Calif.

[*] Notice: The portion of the term of this patent subsequent to Apr. 22, 2003 has been disclaimed.

[21] Appl. No.: 210,688

[22] Filed: Jun. 23, 1988

Related U.S. Application Data

[63] Continuation-in-part of Ser. No. 118,088, Nov. 6, 1987, abandoned, which is a continuation of Ser. No. 790,291, Oct. 22, 1985, Pat. No. 4,713,348, which is a continuation of Ser. No. 482,124, Apr. 5, 1983, Pat. No. 4,584,277.

[51] Int. Cl.$^5$ ............. G01N 33/566; G01N 33/543; G01N 33/544; G01N 33/545
[52] U.S. Cl. .................................. 436/501; 435/7.2; 435/7.1; 435/7.25; 436/518; 436/520; 436/523; 436/528; 436/531; 436/800; 436/805; 436/808; 436/172; 424/11
[58] Field of Search .................. 435/4, 7, 172, 513; 436/501, 519, 520, 824; 442/61

[56] References Cited

U.S. PATENT DOCUMENTS

| | | |
|---|---|---|
| 4,080,264 | 3/1978 | Cohen et al. ............................ 435/7 |
| 4,499,052 | 2/1985 | Fulwyler ............................. 436/172 |
| 4,511,662 | 3/1985 | Baran et al. ......................... 436/513 |
| 4,584,277 | 4/1986 | Ullman ................................ 436/501 |
| 4,727,020 | 2/1988 | Recktenwald . | |

FOREIGN PATENT DOCUMENTS

WO86/04684 8/1986 World Int. Prop. O. .

OTHER PUBLICATIONS

Mirro, J. Jr., J. F. Schwartz, and C. I. Civin, 1981, Simultaneous Analysis of Cell Surface Antigens & Cell Morphology Using Monoclonal Antibodies Conjugated to Fluorescent Microspheres, J. Immo. Meth. 47:39–48.

Primary Examiner—Robert A. Wax
Assistant Examiner—David R. Preston
Attorney, Agent, or Firm—Theodore J. Leitereg; Shelley G. Precivale

[57] ABSTRACT

A method for determining the presence of a specific binding member bound to first particles in a liquid medium is disclosed. The method comprises providing in combination (1) a liquid medium suspected of containing a specific binding member bound to first particles, (2) means for agglutinating the first particles in relation to the presence of the specific binding member, and (3) second particles having the same or a different specific binding member for said means for agglutinating bound thereto, thereby providing for said means to agglutinate the second particles. Agglutination of the first and second particles are separately detectible and distinguishable by spectroscopic measurement. The medium is incubated and agglutination of each of the particles is determined spectroscopically without separating the first and second particles. The agglutination of the first particles is related to the presence of the specific binding member on the first particles, and the absence of agglutination of the first particles taken together with agglutination of the second particles is related to the absence of the specific binding member on the first particles.

36 Claims, No Drawings

MULTIPARAMETER PARTICLE ANALYSIS

CROSS-REFERENCE TO RELATED APPLICATIONS

This application is a continuation-in-part of copending application U.S. Ser. No. 118,088, filed Nov. 6,1987, now abandoned, which in turn is a continuation of U.S. Ser. No. 790,291, filed Oct. 22, 1985, now U.S. Pat. No. 4,713,348, which in turn is a continuation of U.S. Ser. No. 482,124 filed Apr. 5, 1983, now U.S. Pat. No. 4,584,277, the disclosures of the above being incorporated herein by reference.

BACKGROUND OF THE INVENTION

1. Field of the Invention

The continued dependence upon whole blood obtained from individuals for replenishing blood in another person requires the monitoring of large numbers of blood samples for their blood group type. In determining the blood group, one is interested in a number of factors: The particular ABO group; the presence of antibodies to the antigens of the ABO group; and the Rh type. Where each of these factors must be determined independently, a large number of tests are involved. For the most part, hemagglutination tests have been involved in measuring the various factors, which are subjective labor intensive and cumbersome. Furthermore, instruments for automated testing are available but these instruments are expensive and designed for large numbers of tests. It is therefore desirable to find techniques which allow for minimal numbers of determination and automation of the method of determination, while accurately reporting the information necessary for blood typing.

Specific antibodies to cell surface antigens other than the A and B blood group antigens are commonly found in 1-2% of human blood samples. The presence of these antibodies in a blood transfusion recipient may cause an adverse reaction if the blood that is transfused contains cellular antigens complementary to the recipient's antibodies. It is, therefore, necessary to test recipient blood for such antibodies. Normally, this is done by combining the serum or plasma of the recipient with "test cells" that are known to carry the relevant antigens on their surface. After incubation of this mixture, the cells are separated, washed free of the serum or plasma, and incubated with anti-immunoglobulin. This reagent, often called Coombs' reagent, binds to any recipient antibodies that are bound to the cells and causes the cells to agglutinate. Agglutination therefore indicates that the antibody screen is positive. Since the ability of the Coomb's reagent to cause agglutination can be blocked by patient immunoglobulin that is present if washing is incomplete, it is necessary to carry out a positive control when no agglutination of the test cells occurs. This may be done by separating the test cells from the solution containing the anti-immunoglobulin by centrifuging such solution and then adding to the solution "control cells" that are presensitized, that is, they have human antibodies bound to them. Usually, the control cells are prepared by incubating Rh positive cells with anti-Rh antibodies. If patient immunoglobulin has been removed and anti-immune globulin is present, the control cells will agglutinate and the test will be deemed valid. If they do not agglutinate, a negative antibody screen result indicated by the absence of agglutination the test cells is considered invalid.

The above described positive control for antibody screen requires that a solution containing the test cells be centrifuged or that the test cells be otherwise separated from the anti-immunoglobulin solution prior to addition of the control cells. This is considered necessary because of difficulty in observing test cell agglutination in the presence of control cells.

SUMMARY OF THE INVENTION

The present method avoids the difficulty of measuring agglutination of one cell type in the presence of another cell type and therefore permits the test cell positive control for antibody screening to be carried out without first removing the test cells from the suspension medium.

One aspect of the present invention concerns a method for determining the presence of a specific binding member (SBM) in a sample. The method comprises the steps of combining in a liquid medium, an agglutinating agent and particles to which the SBM is suspected of being bound and determining whether agglutination occurs and whether there is sufficient agglutinating reagent present in the medium to cause agglutination. The improvement of the present invention comprises carrying out the agglutinating and determining in one liquid medium without intervening removal (as defined below) of the particles from the medium.

Another aspect of the present invention is concerned with a method for determining the presence of a SBM bound to first particles ($P_1$) in a liquid medium. The method comprises providing in combination (i) a liquid medium suspected of containing SBM bound to $P_1$, (ii) means for agglutinating $P_1$ in relation to the presence of SBM on $P_1$ and (iii) second particles ($P_2$) having SBM or a different specific binding member for means for agglutinating bound thereto, thereby providing for means to agglutinate $P_2$. Agglutination of $P_1$ and $P_2$ are separately detectable and distinguishable by spectroscopic measurement. The medium is incubated and agglutination of each of the particles without separation is determined spectroscopically. Agglutination of $P_1$ is related to the presence of SBM on $P_1$ and agglutination of $P_2$ in the absence of agglutination of $P_1$ is related to the absence of SBM on $P_1$.

Another aspect of the present invention concerns a method for detecting agglutination of two sets of red blood cells. The method comprises providing in combination in a liquid medium two sets of red blood cells and means for agglutinating each set of cells. Agglutinated cells of each of the sets are separately detectable and distinguishable by their spectroscopic properties. The medium is incubated and agglutination of each of the set of particles is determined spectroscopically without separation of the sets of particles or provision for physical localization of individual cells.

Another aspect of the present invention concerns a method of determining an antibody in a blood sample. The method comprises the steps of agglutinating, in a liquid medium by means of an antibody for immunoglobulin, first cells having a surface antigen to which is bound the antibody. Whether the antibody for immunoglobulin is present in excess is determined by using second cells having a surface immunoglobulin. The improvement of the present invention comprises carrying out the agglutinating and determining steps in one liquid medium without intervening separation of the first cells from the medium.

Another aspect of the present invention concerns a method for determining the presence of an antibody in a sample. The sample suspected of containing the antibody is combined in an aqueous medium with first cells having a surface antigen reciprocal to the antibody. The cells are separated from the medium, combined in a second aqueous medium with an antibody for immunoglobulin, and incubated. Second cells having surface immunoglobulins recognizable by the antibody are subsequently added to the medium. At least one of the first or second cells has a fluorescent label. Different labels on different cells are distinguishable by spectroscopic characteristics which are emission, absorption, and light scattering. Agglutination of the first cells and the second cells is determined spectroscopically without separation of the cells from each other or from the second aqueous medium. The agglutination is then related to the presence of the antibody.

DESCRIPTION OF THE SPECIFIC EMBODIMENTS

In accordance with the subject invention, methods are provided for determining agglutination of sets of particles in a medium with a minimum of determinations and separations of the particles from each other or from the medium. The methods have application for detecting agglutination of two sets of particles, for determining the presence of a specific binding member bound to particles, and particularly in the area of blood typing.

Before proceeding further with a description of the specific embodiments, the following terms will be defined.

Specific binding member ("SBM")—one of two different molecules, having an area on the surface or in a cavity which specifically binds to and is thereby defined as complementary with a particular spatial and polar organization of the other molecule. The specific binding member may be a ligand or receptor (antiligand). These will usually be members of an immunological pair such as antigen-antibody, although other specific binding pairs such as biotin-avidin, hormones-hormone receptors, nucleic acid duplexes, IgG-protein A, DNA-DNA, DNA-RNA, and the like are not immunological pairs but are included in the definition of SBM.

Ligand-any organic compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component Clq, and the like.

Particles—the particles are generally at least about 0.02 microns and not more than about 100 microns, usually at least about 0.05 microns and less than about 20 microns, preferably from about 0.3 to 10 microns diameter. The particle may be organic or inorganic, swellable or non-swellable, porous or non-porous, preferably of a density approximating water, generally from about 0.7 to about 1.5 g/ml, and composed of material that can be transparent, partially transparent, or opaque. Normally, the particles will be biologic materials such as cells and microorganisms, e.g., erythrocytes, leukocytes, lymphocytes, hybridomas, streptococcus, staphylococcus aureus, *Escherichia coli*, viruses, and the like.

The particles can also be particles comprised of organic and inorganic polymers, liposomes, latex particles, phospholipid vesicles, chylomicrons, lipoproteins, and the like.

Label—A member of the signal producing system. The label can be isotopic or non-isotopic, usually non-isotopic, including catalysts such as an enzyme, a chromogen such as a fluorescer, dye or chemiluminescer, a radioactive substance, and so forth, preferably a fluorescent dye.

Signal Producing System—The signal producing system may have one or more components, at least one component being a label. The signal producing system generates a signal that can be related to the presence or absence of an SBM in a sample. The signal producing system includes all of the reagents required to produce a measurable signal. Other components of the signal producing system can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, preferably by measurement of electromagnetic radiation.

A large number of enzymes and coenzymes useful in a signal producing system are indicated in U.S. Pat. No. 4,275,149, columns 19 to 23, and U.S. Pat. No. 4,318,980, columns 10 to 14, which disclosures are incorporated herein by reference. A number of enzyme combinations are set forth in U.S. Pat. No. 4,275,149, columns 23 to 28, which combinations can find use in the subject invention. This disclosure is incorporated herein by reference.

The fluorescers of interest will generally emit light at a wavelength above 350 nm, usually above 400 nm and preferably above 450 nm. Desirably, the fluorescers have a high quantum efficiency, a large Stokes shift and are chemically stable under the conditions of their conjugation and use. The term fluorescer is intended to include substances that emit light upon activation by electromagnetic radiation or chemical activation and includes fluorescent and phosphorescent substances, scintillators, and chemiluminescent substances.

Fluorescers of interest fall into a variety of categories having certain primary functionalities. These primary functionalities include 1- and 2-aminonaphthalene, p,p'-diaminostilbenes, pyrenes, quaternary phenanthridine salts, 9-aminoacridines, p,p'-diaminostilbenes, imines, anthracenes, oxacarbocyanine, merocyanine, 3-aminoequilenin, perylene, bis-benzoxazole, bis-p-oxazolyl benzene, 1,2-benzophenazine, retinal, bis-3-aminopyridinium salts, hellebrigenin, tetracycline, sterophenol, benzimidazolylphenylamine, 2-oxo-3-chromen, indole, xanthene, 7-hydroxycoumarin, 4,5-benzimidazoles, phenoxazine, salicylate, strophanthidin, porphyrins, triarylmethanes, flavin and rare earth chelates oxides and salts. Exemplary fluorescers are enumerated in U.S. Pat. No. 4,318,707, columns 7 and 8, the disclosure of which is incorporated herein by reference. Squarine dyes described in U.S. patent application Ser. No. 773,401, filed Sept. 6, 1985 (the relevant disclosure of which is incorporated by reference) are also useful as fluorescers.

A large number of illustrative fluorescers are indicated in U.S. Pat. No. 4,275,149, columns 30 and 31, which disclosure is incorporated herein by reference.

Intervening removal—such removal refers to the separation of particles from a liquid medium such as by decantation, filtration, and the like and also includes centrifugation of the liquid medium to provide a centrifugate comprised of the particles and a supernatant liquid. In the latter instance the supernatant may or may not be physically separated from the centrifugate although the particles are removed from the liquid.

Means for agglutinating—means for causing particles to aggregate. Preferred means include specific binding members that are reciprocal to a specific binding member on a particle to be agglutinated. For example, where a particle contains a particular specific binding member (SBM) such as an antigen or antibody, the complementary specific binding member, preferably an antibody, can be employed to result in agglutination under appropriate conditions. When the SBM is an antibody, a preferred means for agglutinating is antibody for immunoglobulin. Antibodies can be produced by well-known techniques. Conditions for causing agglutination include incubation of the particles in an aqueous medium containing the means for agglutination, preferably with simultaneous gentle mixing to bring the particles into proximity with each other.

As mentioned above one aspect of the present invention involves a method for determining the presence of an SBM bound to first particles ($P_1$) in a liquid medium. A liquid medium suspected of containing SBM bound to $P_1$ is provided in combination with means for agglutinating $P_1$ in relation to the presence of the SBM on $P_1$ and second particles ($P_2$) having the same or a different specific binding member for said means for agglutinating bound thereto, thereby providing for means to agglutinate $P_2$. Agglutination of $P_1$ and $P_2$ are separately detectable and distinguishable by spectroscopic measurement.

The order of combining the above materials will usually provide for the liquid medium suspected of containing SBM bound to $P_1$ to first come into contact with the means for agglutinating $P_1$ and thereafter adding $P_2$ to that mixture. Preferably, the mixture will be incubated with mixing to provide for agglutination of $P_1$ prior to addition of $P_2$. The mixture will then again be incubated with mixing to provide for agglutination of $P_2$. Alternatively, all three materials can be combined simultaneously followed by incubation and mixing.

The medium will normally be aqueous, which may be up to about 40 weight percent of other polar solvents, particularly oxygenated solvents of from 1 to 6, more usually of from 1 to 4 carbon atoms, including alcohols, ethers and the like. Usually, the cosolvents will be present in less than about 20 weight percent. Under some circumstances depending on the nature of the sample, some or all of the aqueous medium could be provided by the sample itself.

After the materials are combined, the medium is incubated. The pH for the medium will usually be in the range of 4-11, more usually 5-10, and preferably in the range of about 6-9. The pH is chosen to maintain a significant level of binding affinity of the binding members to result in agglutination and also for optimal generation of signal by a signal producing system. Various buffers may be used to achieve the desired pH and maintain the pH during the assay. Illustrative buffers include borate, phosphate, carbonate, tris, barbital and the like. The particular buffer employed is not critical, but in individual assays, one buffer may be preferred over another. Moderate, and desirably substantially constant, temperatures are normally employed for the incubation and subsequent steps. The temperatures for the incubation and subsequent determination will generally be in the range of about 4°-50° C., more usually in the range of about 10°-40° C., and frequently will be ambient temperatures, that is, about 15°-25° C.

The concentration, in the liquid sample, of SBM or $P_1$ having SBM which may be determined will generally vary from about $10^{-4}$ to about $10^{-14}$M, more usually from about $10^{-6}$ to $10^{-14}$M. Considerations, such as the concentration of SBM and the protocol will normally determine the concentration of the other reagents.

While the concentrations of many of the various reagents and reagent solutions will generally be determined by the concentration range of interest of the SBM or $P_1$ having SBM, the final concentration of each of the reagents will normally be determined empirically to optimize the sensitivity of the determination over the range of interest. With certain protocols, individual reagents may be used in substantial excess without detrimentally affecting the sensitivity of the assay.

Following the incubation of the medium and particles, agglutination of each of the particles is determined spectroscopically. Generally, at least $P_1$ has a label bound thereto. By choice of label and agglutinating conditions at least two distinguishable signals are generated by the two agglutinated particles respectively. Usually, the signals from the two particles will be emission, absorption and/or light scattering.

The agglutination of $P_1$ is related to the presence of the SBM of $P_1$. The agglutination of $P_2$ in the absence of agglutination of $P_1$ is related to the absence of the SBM on $P_1$.

The method requires that the signal observed with agglutinated particles be different from the signal observed with non-agglutinated particles and that agglutination of $P_1$ gives a different signal than agglutination of $P_2$. Usually, when one particle is unlabeled and is observed by light scatter, it will be present in smaller quantity than the other particle, which will normally be labeled. Alternatively, the other particle can produce a different light scatter because it is a different size. When both particles are labeled with fluorescers, the labels will have different emission and/or absorption maxima or emission lifetimes. In certain cases, the label will naturally be present within the particle as, for example, chemiluminescence of lymphocytes and light absorption of erythrocytes. When the desired signal is light scatter, particles can be selected that have intrinsically high light scatter such as erythrocytes, colloidal metal, colloidal carbon, or colloidal dyes, etc. Labeling of a particle with a dye allows for detection of the labeled particle by absorption or divergence, usually divergence, In one method of detection a sufficiently small volume of the medium in which labeled particles are suspended is monitored such that on the average only one or a few particles will be inspected at a time. In order to determine if aggregation of the particles occurred, a large number of measurements of such measurement volumes can be made, which measurements differ temporally or spatially. When no aggregation has occurred, the number of particles within each volume, and hence the signal, will vary statistically and depend on the measurement volume and the concentration of the particles. When aggregation has occurred the presence of particle aggregates within some measurement volumes will increase the signal from those volumes and the frequency of measurements of signal exceeding a predetermined value will therefore be increased.

The sample will be continuous, being still or stirred or moving, usually moving relative to the measurement volume when the measurements differ temporally. Usually, the measurement volume will be contiguous with, and substantially surrounded by, the suspension medium and will be in a diffusive relationship with the entire sample being measured.

One means for irradiating measurement volumes is to employ a method and apparatus described in U.S. Pat. No. 4,564,598, the disclosure of which is incorporated herein in its entirety by reference thereto. Basically, the measurement volume is irradiated employing an optical fiber where an irradiation volume that encompasses the measurement volume is determined by the construction of the optical fiber. The shape of the irradiation volume will normally be conical. The optical fibers are typically constructed of a core region and at least one cladding region, whose thickness (diameter) and relative refractive indices determine both the half angle of the cone and the cone's smallest diameter at the tip of the fiber. The effective axial length, that is, the length within which the measurement volume is located, is determined by the intensity of the excitation beam, the sensitivity of the detection methods and the rate of drop in intensity of the excitation light with increasing axial distance from the fiber tip. The rate depends upon the half angle of the cone, with larger half angles causing greater rates of intensity drop and, hence, shorter effective cone lengths. Also affecting the intensity drop will be light scattering and absorption properties of the medium.

The various parameters affecting the observed signal are chosen to insure that a measurable signal is available when a particle aggregate is present within the measurement volume, which signal will be significantly greater than the signal produced with no particles in the measurement volume.

Different effective measurement volumes can be provided by allowing for diffusion of particles in and out of the measurement volume. Alternatively, one can have a plurality of optical fibers, each one receiving signals from different irradiation volumes. Alternatively, a dynamic system may be used where the sample flows by one or more optical fibers or one or more optical fibers move through the sample.

The excitation light may be provided by irradiating the entire sample or a major portion of the sample with excitation light. Alternatively, and preferably, the excitation light may be provided by an optical fiber so that the measurement volume will be directly related to the volume irradiated.

The method of the present invention has particular application to the determination of the presence of an antibody in a sample. The method comprises combining in an aqueous medium the sample suspected of containing the antibody with first cells having a surface antigen reciprocal to the antibody. For example, in blood typing one determination involves the presence or absence of antibodies to the Lewis, Kell, and Duffy antigens and also to the Rh or D antigen. The sample may be serum, plasma or whole blood. The first cells having a surface antigen reciprocal to the antibody can be erythrocytes having the complementary antigen to the antibody being detected. The cells are then separated from the medium and combined in a second aqueous medium with antibody for an immunoglobulin. Usually, an incubation period follows. Second cells having surface immunoglobulins recognizable by the antibody for immunoglobulin are then added. At least one of the first or second cells has a fluorescent label and usually each has a different fluorescent label when the sample is whole blood. Different labels and different cells are distinguishable by spectroscopic characteristics, which include emission, absorption, and light scattering. The second aqueous medium is incubated. Agglutination of the first cells and the second cells is determined spectroscopically after each of the incubations or after the final incubation without intervening removal of the cells from the second aqueous medium. The agglutination is related to the presence of the antibody. Agglutination of the first cells indicates the presence of the antibody and agglutination of the second cells in the absence of agglutination of the first cells indicates the absence of the antibody.

As mentioned above, the present invention has particular application to automated blood typing procedures. It is useful in the Coombs antiglobulin test where immunoglobulin-containing plasma is first combined with test cells, which are then removed and carefully washed free of sample immunoglobulin prior to determinating whether antibody from the plasma has become bound to the cells by monitoring for agglutination upon addition of antiglobulin. The present invention allows the use of positive control cells to determine if washing is complete without intervening removal of the test cells from the antiglobulin containing medium or from the control cells.

In such a determination a sample comprising serum or plasma is combined and incubated with test cells that bear a fluorescent label and have surface-bound antigen reciprocal to the antibody to be determined. The test cells are then separated from the medium and washed so that the cells are free from the immunoglobulin from the sample. The test cells are then combined with antibody for immunoglobulin. The medium is incubated and agglutination is then determined. Control cells that have immunoglobulin on the surface are added prior to or following the determination. Preferably, the control cells will not be labeled or will be labeled with a different fluorescer. After another incubation measurement is made of agglutination of the control cells and, where not previously measured, of the test cells without intervening removal of the cells from the second aqueous medium. Agglutination of the test cells indicates the presence of antibody in the sample. Agglutination of the control cells in the absence of agglutination of the test cells indicates the absence of the antibody in the sample.

Failure of the test cells to agglutinate when the antibody to be determined is present can result when immunoglobulin from the sample is present in the medium because of incomplete washing after the initial separation. Control cells are used to determine the completeness of the wash. If the control cells agglutinate, then the initial wash has removed sufficient immunoglobulin to avoid absorption of the added antibody for immunoglobulin. The antibodies for immunoglobulin are therefore available to agglutinate the test cells when immunoglobulin has become bound to the test cells. Consequently, failure of the test cells to agglutinate when the control cells have agglutinated indicates that the antibody to be determined was not in the sample. The agglutination can be carried out in one liquid medium without intervening separation of the test cells from the medium or from the second cells.

Another aspect of the method of the present invention involves detecting agglutination of two sets of red blood cells. Two sets of red blood cells are provided in combination in a liquid medium along with means for agglutinating each set of the cells. Agglutinated cells of each of said sets are separately detectable and distinguishable by their spectroscopic properties. The medium is incubated and the agglutination of each of the sets of cells is determined spectroscopically without separation thereof or without provision for physical localization of individual cells such as that utilized in cell sorting. At least one of the sets of cells has a label, which generally is a fluorophor. The spectroscopic properties are emission and light scatter. Agglutination of one or both of the sets of cells indicates the presence of an agglutinating agent for each, respectively.

Another aspect of the present invention concerns a method for determining the presence of a SBM in the liquid medium. A liquid medium suspected of containing the SBM is provided in combination with (1) first particles having a specific binding member complementary to SBM bound thereto ($SBM_1$-$P_1$), and (2) means for agglutinating $SBM_1$-$P_1$, wherein the means are reactive with SBM; incubating the mixture; and adding second particles having a specific binding member for the means for agglutination bound thereto ($SBM_2$-$P_2$). At least one of $SBM_1$-$P_1$ or $SBM_2$-$P_2$ has a label. The different labels and different particles are distinguishable by spectroscopic characteristics, which are emission, absorption and light scatter.

Referring to the above particular example of the use of test cells in blood typing, the SBM is exemplified by a patient's immunoglobulin. As mentioned above, it is desirable to determine whether all of the patient's immunoglobulin has been removed in the first wash. $SBM_1$-$P_1$ is exemplified by cells having an antigen to which the antibody being determined in the blood typing is attached. $SBM_2$-$P_2$ is exemplified by the control cells and the means for agglutinating is exemplified by antibody to immunoglobulin.

The medium is then incubated and at least a portion of the medium is irradiated with light. The medium is continuous and the particles are suspended in the continuous medium. Populations of particles having electromagnetic signals differing from threshold values are determined and related to the presence of SBM. In one approach the $SBM_1$-$P_1$ is labelled with a fluorophor and the method involves determining emission and light scatter. Agglutination of $SBM_1$-$P_1$ indicates the presence of SBM bound to this particle. Agglutination of $SBM_2$-$P_2$ in the absence of agglutination of $SBM_1$-$P_1$ indicates the absence of SBM bound to $SBM_1$-$P_1$.

For convenience, the reagents for conducting a method in accordance with the present invention can be provided in a kit. The kit comprises the reagents in packaged combination. The reagents are packaged according to their respective reactivities to one another and to insure shelf life. For example, each reagent can be packaged in separate containers or reagents can be combined where co-reactivity will permit. In the area of blood typing the reagents will include test cells carrying a label, control cells, and antibody for immunoglobulin. The kit can also include ancillary materials such as buffers and stabilizers. In addition, other ancillary materials include proteins such as albumins, surfactants, particularly non-ionic surfactants, binding enhancers, e.g., polyalkylene glycols, and the like.

EXAMPLES

The invention is demonstrated further by the following illustrative examples. Parts and percentages are by volume unless indicated otherwise.

EXAMPLE 1

Cell Detection System

The light beam for a He/Ne laser (2 mW, Melles Griot, San Marcos, CA) emitting at 633 nm was focused onto one end of a pure silica optical fiber having a 50 $\mu$m core and a numerical aperture of 0.22. The other end of the fiber was incorporated into a dual fiber probe designed such that the axis of the cone of light emanating from the end of the fiber intersected at a 60° angle with the axis of a second like fiber at a distance of about 225 $\mu$m from the end of each fiber. The collection volume, defined as the overlap of the light cone from the first fiber and the light acceptance cone of the second fiber, was about $10^{-6}$ cm$^3$. The probe was disigned to be immersed directly into the sample to be analyzed. A portion of the light that either was emitted by fluorescent particles or solutes or was scattered from particles within the collection volume could be transmitted by the second fiber and focused through a filter wheel onto a photomultiplier (Hamamatsu, Bridgewater, NJ). The filter wheel contained a 633 nm bandpass filter for detection of scattered light and a tandem pair of 645 nm long-pass filters for detection of fluorescent light. The photomultiplier output was processed through a preamplifier and discriminator (Pacific Instruments, Concord, CA) resulting in a photopulse output suitable for photon counting. Photopulses were counted over 500 $\mu$s gate times and the count passed to an on-line microprocessor. Fluctuations of the counts in sequential gate times were used to estimate the degree of aggregation of particles.

SAMPLE TRANSPORT AND MIXING

Samples and reagents were combined in a single drop on a flat sheet of latex rubber held in contact with the upper surface of a temperature-controlled reaction block. Within the block underlying the latex sheet were cup-shaped cavities that were about 1 cm in diameter that were each connected to a vacuum line through a 1 mm opening at the bottom. Efficient mixing of the drops was achieved by alternately evacuating the cups to cause a section of the sheet to be stretched and drawn downward, and releasing the vacuum to permit the sheet to return to its original position. With sufficiently small liquid volumes, the drops of reaction mixtures remained in place by surface tension and could be transported across a series of cavities by moving the sheet during periods when no vacuum was applied. This permitted the addition and removal of reagents at different locations and made it possible to simultaneously process a series of samples. The final cavity in the series was positioned under the dual fiber probe which was equipped with a dispenser for dilution of the cells and could be moved vertically to permit immersion into the suspension.

Dyes 1-3-bis [4-dibutylamino-2-hydroxyphenyl]-2,4-dihydroxycyclobutenediylium dihydroxide, bis (inner salt)

(TBS) was used to stain red blood cells. The dye was synthesized by the method of Sprenger and Ziegebein, *Angew. Chem., Internat. Edit.* (1966) 5: 894, by refluxing one equivalent of squaric acid with two equivalents of N,N-dibutylaniline in a 2:1 mixture of n-butanol and benzene with continuous azeotropic removal of water. On cooling, the products separated as green crystals which were collected by filtration and washed with methanol. The dyes were recrystallized from a 1:1 mixture of methanol and methylene chloride. The absorption maximum of the dye in dimethylformamide was 650 nm, $\epsilon = 330,000$ $M^{-1}$ $cm^{-1}$.

Antibody Reagents

Anti-human IgG was prepared from the serum of rabbits immunized with human IgG (Mollison, "Blood Transfusion in Clinical Medicine" (7th edition), Blackwell Scientific Publications (1983), 505-508. The IgG fraction was isolated by ammonium sulfate precipitation and ion exchange chromatography (DEAE-Sephacell) and diluted in 20 mM Tris-saline buffer to 11-18 mg/mL with 1.25% PVP.

Reagent Red Blood Cells

For antibody screening, cells were obtained from three different donors which were selected such that each of the approximately 20 clinically significant antigens were represented on one or more of the cells. The cells were washed with saline and suspended to approximately $2 \times 10^9$ cells/mL in saline containing 2% BSA. Fifty μL of $10^{-4}$M TBS in dimethylacetamide were added to one mL of this suspension and the mixture was gently mixed for 15-30 minutes at room temperature. The cells were then washed with saline and stored at 4° C. in an isotonic cell medium (pH 8.3) (Uda, et al., *Transfusion* (A85) 25:325-329) at a final concentration of 5% (v/v) for reverse grouping cells and 10% for antibody screening cells.

Control cells used for the antibody screen (Uda, et al., supra) were prepared by incubating Rh(D) positive cells with a human monoclonal anti-Rh(d) antibody (Bioresponse, 0.24 μg/mL) in saline with 2% BSA for 45 minutes at 37° C. The antibody coated cells were washed in saline and stored in cell medium (Widmann, et. "Technical Manual," 9th ed., Arlington, VA, American Association of Blood Banks (1985) 376) at a concentration of 10% (v/v).

Ferrofluid

Colloidal magnetizable magnetite was prepared by a modification of the procedure described by Massart (IEEE Transactions on Magnetics, MAG 17 (1981) 1247). Equal volumes of 1.5M ammonium hydroxide and an aqueous solution containing 0.16M $FeCl_3$, 0.08M $FeCl_2$, and 0.08M HCl at room temperature were pumped into a flask over a 5 minute period. After the addition was complete, the magnetite was allowed to settle for one hour and the supernatant, which represented about 80% of the total volume, was decanted. The concentrated slurry of magnetite and an equal volume of 2.0M perchloric acid were simultaneously pumped into a second flask. The suspended material was separated magnetically. Upon addition of one-fifth the original volume of water, a colloidal dispersion was obtained which was dialyzed against 10 mM perchloric acid. The resulting suspension contained 44 mg/mL of iron as determined by addition of an equal volume of concentrated hydrochloric acid and assaying according to the method of Persijn, et al. (*Clinica Chimica Acta* (1971) 35: 91-98).

Succinylated BSA was prepared by adding 2.5 mL of 0.5M succinic anhydride (Aldrich) in dimethylformamide (Mallinckrodt) to 5.0 g of BSA (crystalline grade, Miles Laboratories) in 250 mL of 0.1M sodium phosphate, pH 8.0, at room temperature. After 1.5 hours, the solution was dialyzed exhaustively against deionized water. The electrophoretic mobility of the modified protein was 1.75 (native BSA=1.00), determined by agarose gel electrophoresis (Paragon, SPE, Beckman).

The colloidal iron oxide was diluted with water to 10 mg/mL (pH 2.9) and 100 mL of this suspension was combined with an equal volume of succinylated BSA (9.5 mg/mL, adjusted to pH 3.3 with 0.1M $HClO_4$). The pH of the solution was then raised to 9.0 by the rapid addition of 15-20 mL of 0.1M tetramethylammonium hydroxide. During this process, the clear, dark-brown liquid became cloudy and then clarified again. The average particle size was determined by dynamic scattering spectrometry (Nicomp Instruments, Model HM5-90) to be 55-65 nm. A portion of the ferrofluid preparation was concentrated 5-fold by membrane ultrafiltration (Amicon) to prepare a 25 mg/mL reagent.

Other Reagents

Saline was an aqueous solution of 0.15 NaCl. Low-ionic-strength-solution (LISS) was an isotonic phosphate-buffered glycine solution containing 0.03M NaCl, pH 6.7. Polyacrylic acid (Aldrich, ave. MW=5000) was diluted to 5 mg/mL in 0.1M glycine buffer, pH 8.0. Polyvinylpyrrolidone (PVP) (GAF) was K-60, non-pharmaceutical grade. Polybrene® (hexadimethrine bromide, Aldrich, ave MW=4300) was a 16 mg/mL solution in LISS, pH 6.7.

Automated Antibody Screening

Plasma was first removed from the blood to be tested by mixing 0.5 mL of blood, 40 μL of 25 mg/mL ferrofluid, 200 μL of LISS, and 40 μL of polybrene in a 1 cm square cup. The cell-ferrofluid coaggregates were separated by positioning like poles of two 2.1 kgauss magnets as close as possible to adjacent sides of the cup.

The cell-free plasma was removed and tested against three different sets of stained reagent red blood cells. For each test, 10 μL of cells and 100 μL of plasma were mixed for 9 minutes on the latex sheet at a reaction block temperature of 37° C. Twenty microliters of ferrofluid (5 mg/mL), 20 μL of polybrene, and 50 μL LISS were then added and the cells magnetically separated. The liquid was removed and the cells washed with LISS and resuspended by addition of 15 μL of polyacrylic acid. Anti-human IgG reagent (20 μL) was then added and the cell suspension was mixed for 1 minute. Next, control cells (10 μL) were added, and after 1 minute of incubation, the sample was diluted with 0.5 mL of saline. The resulting suspension was analyzed sequentially for agglutination of the reagent cells (fluorescence) and the control cells (light scatter).

Interpretation of Results

Agglutination of erythrocytes was determined by drawing the cell suspension past the end of the dual fiber probe and monitoring the fluorescence or light scatter in multiple sample volumes defined by 500 μs gate times. Continuous measurements were recorded for 10 seconds. The data were analyzed for first identifying series of sequential gate times that had light pulse counts in excess of a threshold value and were therefore attributed to the passage of one or more cells past the probe. Signal pulses were usually about 3-4 gate times (1.5-2 ms) depending on the rate of motion of the liquid. These events were counted to provide an "agglutination index." For the purpose of distinguishing an agglutinated from a nonagglutinated sample, "cut-off" agglutination index values were obtained by testing known samples.

In the antibody screen test, increased fluctuations in the fluorescent signal above a "cut-off" agglutination index were attributed to agglutination of the stained cells. The fluorescence signal was monitored by using the 645 nm long-pass filter. The antibody screen control cells were not stained, and agglutination was therefore monitored by measurement of fluctuations in the light scatter signal using the 633 nm band-pass filter. Since these cells were coated with human IgG, their agglutination served as an indicator that enough anti-human IgG had been added. Thus, a sample that tested negative in the antibody screen was considered to be indeterminant unless agglutination of the control cells was detected by light scatter fluctuations.

RESULTS

Automated Testing

The automated antibody screen was performed on 103 specimens that were either fresh blood or were "reconstituted" samples prepared by mixing antibody-positive plasma (stored frozen) with compatible red blood cells to stimulate a positive sample. The samples had a broad range of titers of antibodies to a variety of clinically significant antigens. In the automated method, plasma obtained by magnetic separation was tested against a panel of three sets of antibody screen reagent cells. Each sample was also tested with the same reagent cells using standard manual techniques and reagents. The results are summarized in Table 1. Two of 26 samples that tested negative by the manual method were positive by automated testing, and 7 of 77 samples that were positive by the manual method were negative by the automated method. The seven samples that were missed by the automated method produced very weak but reproducible agglutination by manual testing. The one indeterminate sample failed to show a light scatter signal from the control cells, due presumably to incomplete removal of IgG during washing of the cells.

TABLE 1

Correlation between manual and automated antibody screening of 103 patient samples.

| Manual Determination | Automated Screen (No. of Samples) | | |
|---|---|---|---|
| | Positive | Negative | Indeterminate[a] |
| Positive | 69 | 7 | 1 |
| Negative | 2 | 24 | 0 |

[a] Lack of agglutination of the control cells.

The present method takes advantage of the clinically proven agglutination chemistry while providing novel separation, sample handling, and detection methods to permit automation and objective interpretation. The method permits antibody screening involving the use of test cells and control cells to be carried out without the need for a separation step such as centrifugation, decantation, and the like.

Although the foregoing invention has been described in some detail by way of illustration and example for purposes of clarity of understanding, it will be obvious that certain changes and modifications may be practiced within the scope of the appended claims.

What is claimed is:

1. A method for determining the presence of a specific binding member (SBM) bound to first particles ($P_1$) in a liquid medium, said method comprising:

providing sequentially in combination (1) a liquid medium suspected of containing SBM bound to $P_1$, (2) means for agglutinating $P_1$ in relation to the presence of said SBM on $P_1$, and (3) second particles ($P_2$) having the same or a different specific binding member for said means for agglutinating bound thereto, thereby providing for said means to agglutinate $P_2$, wherein agglutination of $P_1$ and $P_2$ are separately detectible and distinguishable by spectroscopic measurement;

incubating said medium;

determining spectroscopically agglutination of each of said particles without separation of $P_1$ from $P_2$; and relating said agglutination of $P_1$ to the presence of said SBM on $P_1$ and agglutination of $P_2$ in the absence of agglutination of $P_1$ to the absence of said SBM on $P_1$.

2. The method of claim 1 wherein said SBM is an immunoglobulin.

3. The method of claim 1 wherein said first particles are cells having a surface antigen with an antibody bound thereto.

4. The method of claim 1 wherein said means for agglutinating is antibody for immunoglobulin.

5. The method of claim 1 wherein said second particles are cells having surface immunoglobulins.

6. The method of claim 1 wherein said first particle has a label bound thereto.

7. The method of claim 6 wherein said label is a fluorophor.

8. The method of claim 1 wherein said determining involves emission and light scatter.

9. A method for detecting agglutination of two sets of red blood cells, which method comprises:

providing sequentially in combination in a liquid medium one set of red blood cells and means for agglutinating said set of said cells, and a second set of cells, wherein agglutinated cells of each of said sets are separately detectible and distinguishable by their spectroscopic properties;

incubating said medium; and determining spectroscopically agglutination of each of said sets of cells without separation thereof or provision for physical localization of individual cells.

10. The method of claim 9 wherein at least one of said set of cells has a label.

11. The method of claim 10 wherein said label is a fluorophor.

12. The method of claim 9 wherein said spectroscopic properties are emission and light scatter.

13. A method for determining the presence of an antibody in a sample, said method comprising:

combining in an aqueous medium a sample suspected of containing an antibody of interest with first cells having a surface antigen reciprocal to said antibody;

separating said cells from said medium;

combining in a second aqueous medium said cells and an antibody for an immunoglobulin, incubating said second aqueous medium and adding to it second cells having surface immunoglobulins recognizable by said antibody for an immunoglobulin wherein at least one of said first or second cells has a fluorescent label, different labels and different cells being distinguishable by spectroscopic characteristics, which are emission, absorption, and light scattering, determining spectroscopically agglutination of said first cells and said second cells without separation of said cells from each other or from said second aqueous medium; and relating said agglutination to the presence of said antibody of interest.

14. The method of claim 13 wherein said antibody is selected from the group consisting of immunoglobulins specific to human erythrocyte surface antigens.

15. The method of claim 13 wherein said immunoglobulins on said second cells have the same binding properties as said antibody in said sample.

16. The method of claim 13 wherein said fluorescent label is selected from the group consisting of fluorecein and rhodamine derivatives, phycobiliproteins, squaraines, umbelliferones, cyanines and merocyanines.

17. The method of claim 13 wherein said first and second cells have different fluorescent labels bound thereto.

18. The method of claim 13 wherein said first cells are labeled and said determining involves emission and light scatter.

19. In a method for determining the presence of a specific binding member (SBM) in a sample, said method comprising the steps of agglutinating in a liquid medium, by means of an agglutinating agent, particles to which said SBM have been bound and determining whether said agglutinating reagent is present in said medium after said agglutination, the improvement which comprises carrying out said agglutinating and said determining in one liquid medium without intervening separation of said particles from said medium.

20. The method of claim 19 wherein said determining comprises adding to said liquid medium a second set of particles that are agglutinated during said method.

21. In a method for determining an antibody in a blood sample, said method comprising the steps of agglutinating, in a liquid medium by means of an antibody for immunoglobulin, first cells having a surface antigen to which is bound said antibody, and determining whether said antibody for immunoglobulin is present in excess by using second cells having surface immunoglobulin, the improvement which comprises carrying out said agglutinating and said determining in one liquid medium without intervening separation of said first cells from said medium.

22. The method of claim 21 wherein said determining comprises adding to said liquid medium a second set of particles that are agglutinated during said method.

23. A method for determining the presence of a specific binding member (SBM) in a liquid medium, said method comprising:

providing in combination in sequence a liquid medium suspected of containing SBM, (1) first particles having a specific binding member bound thereto ($SBM_1$-$P_1$), (2) means for agglutinating $SBM_1$-$P_1$, said means being reactive with SBM, and (3) second particles having a specific binding member for said means for agglutinating bound thereto ($SBM_2$-$P_2$), wherein at least one of $SBM_1$-$P_1$ or $SBM_2$-$P_2$ has a label, different labels and different particles being distinguishable by spectroscopic characteristics, which are emission, absorption and light scatter;

incubating said medium;

irradiating at least a portion of said medium with light, wherein said medium is continuous and said particles are suspended in said continuous medium and determining populations of particles having electromagnetic signals differing from threshold values; and relating said populations to the presence of SBM.

24. The method of claim 23 wherein said SBM is an immunoglobulin.

25. The method of claim 23 wherein said first particles are cells having a surface antigen with an antibody bound thereto.

26. The method of claim 23 wherein said means for agglutinating is antibody for immunoglobulin.

27. The method of claim 23 wherein said second particles are cells having a surface immunoglobulin.

28. The method of claim 23 wherein both first and second particles have a label bound thereto.

29. The method of claim 23 wherein said label is a fluorophor.

30. The method of claim 29 wherein said $SBM_1$-$P_1$ is labeled with a fluorophor and said determining involves emission and light scatter.

31. A method for determining the presence of an antibody in a blood sample, said method comprising:

combining a sample suspected of containing an antibody of interest with first cells having a surface antigen reciprocal to said antibody;

separating said cells from said medium;

combining in a liquid medium said cells and an antibody for an immunoglobulin, incubating said medium and adding to said medium second cells having surface immunoglobulin, wherein at least one of said first or second cells has a fluorescent label, different labels and different cells being distinguishable by spectroscopic characteristics, which are emission, absorption, and light scattering, incubating said medium;

irradiating at least a portion of said medium with light, wherein said medium is continuous and said cells are suspended in said continuous medium, and determining populations of cells having electromagnetic signals differing from threshold values; and relating said populations to the presence of said antibody.

32. The method of claim 31 wherein said antibody is selected from the group consisting of immunoglobulins specific to human erythrocyte surface antigens.

33. The method of claim 31 wherein said surface immunoglobulin on said second cells has the same binding properties relative to said antibody for an immunoglobulin as said antibody in said blood sample.

34. The method of claim 31 wherein said fluorescent label is selected from the group consisting of fluorescein and rhodamine derivatives, phycobiliproteins, squaraine dyes, umbelliferones, cyanines, and merocyanines.

35. The method of claim 31 wherein said first and second cells have different fluorescent labels bound thereto.

36. The method of claim 35 wherein said first cells are labeled and said determining involves emission and light scatter.

* * * * *